US007521932B2

(12) United States Patent
Carter, III et al.

(10) Patent No.: US 7,521,932 B2
(45) Date of Patent: Apr. 21, 2009

(54) METHOD AND SYSTEM FOR ADJUSTING THE FUNDAMENTAL SYMMETRIC MODE OF COUPLED HIGH TEMPERATURE SUPERCONDUCTOR COILS

(75) Inventors: Charles F. Carter, III, Wilmington, DE (US); Daniel B. Laubacher, Wilmington, DE (US); James D. McCambridge, Swarthmore, PA (US); Charles Wilker, Wilmington, DE (US); Jiunn Sheng, Newark, DE (US)

(73) Assignee: The Penn State Research Foundation, University Park, PA (US)

( * ) Notice: Subject to any disclaimer, the term of this patent is extended or adjusted under 35 U.S.C. 154(b) by 120 days.

(21) Appl. No.: 10/835,345

(22) Filed: Apr. 29, 2004

(65) Prior Publication Data

US 2005/0046420 A1    Mar. 3, 2005

Related U.S. Application Data

(60) Provisional application No. 60/468,220, filed on May 6, 2003, provisional application No. 60/498,045, filed on Aug. 27, 2003, provisional application No. 60/541,144, filed on Feb. 2, 2004.

(51) Int. Cl.
*G01V 3/00* (2006.01)
(52) U.S. Cl. .................................... 324/318; 324/322
(58) Field of Classification Search ......... 324/300–322; 310/328, 323; 438/29–32; 347/107; 400/120
See application file for complete search history.

(56) References Cited

U.S. PATENT DOCUMENTS

| | | | |
|---|---|---|---|
| 3,373,348 A | 3/1968 | Vanier et al. | |
| 3,530,374 A | 9/1970 | Waugh et al. | |
| 3,764,892 A | 10/1973 | Rollwitz | |
| 4,072,768 A | 2/1978 | Fraser et al. | |
| 4,514,691 A | 4/1985 | De Los Santos et al. | |
| 5,036,279 A | 7/1991 | Jonsen | |
| 5,135,908 A | 8/1992 | Yang et al. | |
| 5,206,592 A | 4/1993 | Buess et al. | |
| 5,233,300 A | 8/1993 | Buess et al. | |
| 5,258,710 A | 11/1993 | Black et al. | |
| 5,262,394 A | 11/1993 | Wu et al. | |
| 5,276,398 A | 1/1994 | Withers et al. | |
| 5,351,007 A | 9/1994 | Withers et al. | |
| 5,418,213 A | 5/1995 | Tanaka et al. | |
| 5,457,385 A | 10/1995 | Sydney et al. | |
| 5,565,778 A * | 10/1996 | Brey et al. | 324/318 |
| 5,583,437 A | 12/1996 | Smith et al. | |
| 5,585,723 A | 12/1996 | Withers | |
| 5,592,083 A | 1/1997 | Magnuson et al. | |
| 5,594,338 A | 1/1997 | Magnuson | |
| 5,656,937 A | 8/1997 | Cantor | |
| 5,661,400 A | 8/1997 | Plies et al. | |
| 5,750,473 A | 5/1998 | Shen | |
| 5,751,146 A | 5/1998 | Hrovat | |
| 5,804,967 A | 9/1998 | Miller et al. | |
| 5,814,987 A | 9/1998 | Smith et al. | |
| 5,814,989 A | 9/1998 | Smith et al. | |
| 5,814,992 A | 9/1998 | Busse-Gravitz et al. | |
| 5,872,080 A | 2/1999 | Arendt et al. | |
| 5,952,269 A | 9/1999 | Ma et al. | |
| 5,973,495 A | 10/1999 | Mansfield | |
| 5,986,455 A | 11/1999 | Magnuson | |
| 5,999,000 A | 12/1999 | Srinivasan | |
| 6,025,719 A * | 2/2000 | Anderson | 324/318 |
| 6,054,856 A | 4/2000 | Garroway et al. | |
| 6,088,423 A | 7/2000 | Krug et al. | |
| 6,091,240 A | 7/2000 | Smith et al. | |
| 6,104,190 A | 8/2000 | Buess et al. | |
| 6,108,569 A | 8/2000 | Shen | |
| 6,150,816 A | 11/2000 | Srinivansan | |
| 6,166,541 A | 12/2000 | Smith et al. | |
| 6,169,399 B1 * | 1/2001 | Zhang et al. | 324/318 |
| 6,194,898 B1 | 2/2001 | Magnuson et al. | |
| 6,201,392 B1 * | 3/2001 | Anderson et al. | 324/300 |
| 6,218,943 B1 | 4/2001 | Ellenbogen | |
| 6,242,918 B1 | 6/2001 | Miller et al. | |
| 6,291,994 B1 | 9/2001 | Kim et al. | |
| 6,335,622 B1 * | 1/2002 | James et al. | 324/318 |
| 6,370,404 B1 | 4/2002 | Shen | |
| D459,245 S | 6/2002 | Power | |

(Continued)

FOREIGN PATENT DOCUMENTS

EP    0 426 851    5/1991

(Continued)

OTHER PUBLICATIONS

Roemer et al., "The NMR Phased Array", Mag Reson Med 16, p. 192-225 (1990).*

(Continued)

*Primary Examiner*—Brij B Shrivastav
(74) *Attorney, Agent, or Firm*—Gifford, Krass, Sprinkle, Anderson & Citkowski, P.C.

(57) ABSTRACT

The frequency of the fundamental symmetric mode of two or more coupled essentially identical high temperature superconductor coils can be tuned, with little degradation in Q, by mechanically displacing the two or more coils with respect to one another. These coupled coils are useful in a detection system for detecting frequencies.

10 Claims, 6 Drawing Sheets

U.S. PATENT DOCUMENTS

| | | |
|---|---|---|
| 6,420,872 B1 | 7/2002 | Garroway et al. |
| 6,478,434 B1 * | 11/2002 | Streetman et al. ............ 359/872 |
| 6,486,838 B1 | 11/2002 | Smith et al. |
| 6,503,831 B2 * | 1/2003 | Speakman .................. 438/674 |
| 6,538,445 B2 | 3/2003 | James et al. |
| 6,541,966 B1 | 4/2003 | Keene |
| 6,556,013 B2 | 4/2003 | Withers |
| 6,566,873 B1 | 5/2003 | Smith et al. |
| 6,590,394 B2 * | 7/2003 | Wong et al. .................. 324/318 |
| 6,617,591 B1 | 9/2003 | Simonson et al. |
| 6,653,917 B2 | 11/2003 | Kang et al. |
| 6,751,489 B2 | 6/2004 | Shen |
| 6,751,847 B1 | 6/2004 | Brey et al. |
| 6,777,937 B1 | 8/2004 | Miller et al. |
| 6,822,444 B2 | 10/2004 | Lai |
| 6,819,109 B2 | 11/2004 | Sowers et al. |
| 6,847,208 B1 | 1/2005 | Crowley et al. |
| 6,952,163 B2 | 10/2005 | Muey et al. |
| 6,956,476 B2 | 10/2005 | Buess et al. |
| 6,958,608 B2 | 10/2005 | Takagi et al. |
| 7,049,814 B2 | 5/2006 | Mann |
| 7,106,058 B2 * | 9/2006 | Wilker et al. ................ 324/300 |
| 7,148,684 B2 * | 12/2006 | Laubacher et al. ........... 324/300 |
| 7,196,454 B2 * | 3/2007 | Baur et al. ............. 310/323.01 |
| 7,265,550 B2 * | 9/2007 | Laubacher et al. ........... 324/318 |
| 7,279,896 B2 * | 10/2007 | Alvarez et al. ............... 324/310 |
| 7,279,897 B2 * | 10/2007 | Alvarez et al. ............... 324/310 |
| 7,332,910 B2 * | 2/2008 | Laubacher et al. ........... 324/318 |
| 2002/0068682 A1 | 6/2002 | Shen |
| 2002/0153891 A1 | 10/2002 | Smith et al. |
| 2002/0156362 A1 | 10/2002 | Bock et al. |
| 2002/0169374 A1 | 11/2002 | Jevtic |
| 2002/0190715 A1 | 12/2002 | Marek |
| 2003/0020553 A1 | 1/2003 | Gao et al. |
| 2003/0062896 A1 | 4/2003 | Wong et al. |
| 2003/0071619 A1 | 4/2003 | Sauer et al. |
| 2003/0119677 A1 | 6/2003 | Qiyan et al. |
| 2003/0136920 A1 | 7/2003 | Flores et al. |
| 2004/0124840 A1 | 7/2004 | Reykowski |
| 2004/0222790 A1 | 11/2004 | Karmi et al. |
| 2004/0251902 A1 | 12/2004 | Takagi et al. |
| 2005/0104593 A1 | 5/2005 | Laubacher et al. |
| 2005/0122109 A1 | 6/2005 | Wilker et al. |
| 2005/0140371 A1 | 6/2005 | Alvarez et al. |
| 2005/0146331 A1 | 7/2005 | Flexman et al. |
| 2005/0206382 A1 | 9/2005 | Laubacher et al. |
| 2005/0248425 A1 | 11/2005 | Alvarez |
| 2005/0258831 A1 | 11/2005 | Alvarez |
| 2005/0264289 A1 | 12/2005 | Alvarez |
| 2005/0270028 A1 | 12/2005 | Alvarez et al. |
| 2006/0012371 A1 | 1/2006 | Laubacher et al. |
| 2006/0038563 A1 | 2/2006 | Cisholm et al. |
| 2006/0082368 A1 | 4/2006 | McCambridge |
| 2006/0119360 A1 | 6/2006 | Yamamoto et al. |

FOREIGN PATENT DOCUMENTS

| | | |
|---|---|---|
| EP | 1 122 550 A1 | 8/2001 |
| EP | 1 168 483 | 1/2002 |
| EP | 1 416 291 | 5/2004 |
| EP | 1 477 823 A | 11/2004 |
| GB | 2 286 248 | 8/1995 |
| GB | 2 289 344 | 11/1995 |
| JP | 05 269 108 | 10/1993 |
| JP | 07 265 278 | 10/1995 |
| WO | WO 92/17793 | 10/1992 |
| WO | WO 92/17794 | 10/1992 |
| WO | WO 92/19978 | 11/1992 |
| WO | WO 92/21989 | 12/1992 |
| WO | WO 94/05022 | 3/1994 |
| WO | WO 95/34096 | 12/1995 |
| WO | WO 96/39636 | 12/1996 |
| WO | WO 96/39638 | 12/1996 |
| WO | WO 98/37438 | 8/1998 |
| WO | WO 98/54590 | 12/1998 |
| WO | WO 99/45409 | 9/1999 |
| WO | WO 99/50689 | 10/1999 |
| WO | WO 00/70356 | 11/2000 |
| WO | WO 02/082115 A2 | 10/2002 |
| WO | WO 02/098364 | 12/2002 |
| WO | WO 03/014700 | 2/2003 |
| WO | WO 03/040761 | 5/2003 |
| WO | WO 03/096041 | 11/2003 |
| WO | WO 2004/001454 A | 12/2003 |
| WO | WO 2004/102596 | 11/2004 |
| WO | WO 2005/059582 A1 | 6/2005 |

OTHER PUBLICATIONS

Ho, D.F. et al., "Metal detector based on high-Tc RF SQUID", Physica C 378-381 (2002) pp. 1404-1407.

Miller, et al., "Performance of a High-Termperature Superconducting Probe for In Vivo Microscopy at 2.0 T", Magnetic Resonance in Medicine, (1999) pp. 72-79, vol. 41.

W.H. Wong, et al., "HTS Coils for High Resolution Nuclear Magnetic Resonance Spectroscopy", Advances in Cryogenic Engineering, (1996), pp. 953-959, New York.

Bendall, et. al., "Elimination of Coupling between Cylindrical Transmit Coils and Surface-Receive Coils for in Vivo NMR" Magnetic Resonance in Medicine v3 p. 157-163. 1986.

Black, et al., "A High-Temperature Superconducting Receiver For Nuclear Magnetic Resonance Microscopy", Science, vol. 259, pp. 793-795 Feb. 5, 1993.

Black, et al., "Performance Of A High-Temperature Superconducting Resonator For High-Field Imaging", Journal Of Magnetic Resonance, pp. 74-80 (1995).

Colton, et al., "Making the World a Safer Place", Science, v.299, i.5611, Pgd.1324-1325, Feb. 2006.

Fisher, et al., "A Versatile Computer-Controlled Pulsed Nuclear Quadrupole Resonance Spectrometer", Review of Scientific Instruments, v70, No. 12, p. 4678, Dec. 1999.

Hill, "Improved Sensitivity of NMR Spectroscopy Probes By Use Of High-Temperature Superconductive Detection Coils", IEEE Transactions On Applied Superconductivity, vol. 7, pp. 3750-3753, Jun. 1997.

Withers, et al., "Thin-Film HTD Probe Coils For Magnetic-Resonance Imaging", IEEE Transactions On Applied Superconductivity, vol. 3, pp. 2450-2453, Mar. 1993.

Landers, et al., "Electronic Effects and Molecular Motion in β-Octahydro-1,3,5,7-tetranitro-1,3,5,7-tetrazocine Bases on $^{14}$N Nuclear Quadrupole Resonance Spectroscopy", American Chemical Society, J. Phys. Chem., 85, pp. 2618-2623, 1981.

Karpowicz, et Al., "Librational Motion of Hexahydro-1,3,5-trinitro-s-triazine Based on the Temperature Dependence of the Nitrogen-14 Nuclear Quadrupole Resonance Spectra: The Relationship to Condensed-Phase Thermal Decomposition", American Chemical Society, J. Phys. Chem. 87, pp. 2109-2112, 1983.

Volpicelli, et. al., "Locked rf Spectrometer for Nuclear Quadrupole Resonance", The Review of Scientific Instruments, v.25, No. 2, pp. 150-153, Feb. 1965.

Benedek, et. al., "Precise Nuclear Resonance Thermometer", The Review of Scientific Instruments, v.28, No. 2, pp. 92-95, Feb. 1957.

Ernst, "Magnetic Resonance with Stochastic Excitation", Journal of Magnetic Resonance 3, pp. 10-27, 1970.

Klainer, et. al., "Fourier Transform Nuclear Quadrupole Resonance Spectroscopy", Fourier, Hadamard, and Hilbert Transforms in Chemistry, pp. 147-182, 1982.

V. Kotsubo et al., "Cryogenic System for a High Temperature Superconductor NMR Probe", Advances in Cryogenic Engineering, Jul. 17, 1995, vol. 41, pp. 1857-1864, New York.

Kushida, et al., "Dependence on the Pure Quadrupole Resonance Frequency on Pressure and Temperature", Physical Review, (Dec. 1956), pp. 1364-1377, vol. 104, No. 5, Massachusetts.

Vanier, "Temperature Dependence of the Pure Nuclear Quadrupole Resonance Frequency in KC103", Canadian Journal of Physics, (Nov. 1960), pp. 1397-1405, vol. 38, No. 11, Canada.

Smith, et al., "Nitrogen Electric Quadrupole and Proton Magnetic Resonances in Thiourea", Journal of Chemical Physics, (Oct. 1964), pp. 2403-2416, vol. 41, No. 8, New York.

Turner, C.W., High temperature superconductor circuit components for cryogenic microwave systems, Electrical and Computer Engineering, 1993, Canadian Conference on Vancouver, BC Canada (Sep. 14-17, 1993) XP 010118071.

W. A. Edelstein et al., A signal-to-noise calibration procedure for NMR imaging systems, Medical Physics, vol. 11 (2) Mar./Apr. 1984, pp. 180-185.

Hirschfeld, et al., "Short Range Remote NQR Measurements", Journal of Molecular Structure, 1980, pp. 63-77, vol. 58, The Netherlands.

Garroway, et al., "Remote Sensing By Nuclear Quadrupole Resonance", IEEE Transactions on Geoscience and Remote Sensing, Jun. 2001, pp. 1108-1118, vol. 39, No. 6.

Garroway, et al., "Narcotics and Explosives Detection by 14N pure NQR", SPIE, 1993, pp. 318-327, vol. 2092, Maryland.

Charles Wilker, "HTS Sensors for NQR Spectroscopy", vol. 1, pp. 143-146, 2004.

Anders Stensgaard, "Optimized Design of the Shielded-Loop Resonator", Journal of Magnetic Resonance, 122, 120-126 (1996), Article No. 0187.

* cited by examiner

METHOD AND SYSTEM FOR ADJUSTING THE FUNDAMENTAL SYMMETRIC MODE OF COUPLED HIGH TEMPERATURE SUPERCONDUCTOR COILS

This application claims the benefit of U.S. Provisional Applications No. 60/468,220, filed May 6, 2003; 60/498,045, filed Aug. 27, 2003; and 60/541,144, filed Feb. 2, 2004; each of which is incorporated in its entirety as a part hereof for all purposes.

FIELD OF THE INVENTION

This invention relates to a method for tuning the resonance frequencies of two or more coupled high temperature superconductor ("HTS") self-resonant coils by mechanically displacing the two or more coils with respect to one another. This invention also relates to a detection system containing such coupled coils.

BACKGROUND OF THE INVENTION

The use of HTS coils in obtaining nuclear magnetic resonance spectra and in magnetic resonance imaging has resulted in substantial gains in signal-to-noise ratios. See, for example, Wong et al, *Advances in Cryogenic Engineering*, 42B, pages 953-959 (1997); and Miller et al, *Mag. Reson. Med.*, 41, pages 72-79 (1999). For many applications it is advantageous to be able to tune the self-resonance frequency of these coils.

An object of the present invention is to provide method and apparatus related to tuning the resonant frequencies of high temperature superconductor (HTS) coils.

SUMMARY OF THE INVENTION

This invention provides a method for tuning the resonance frequencies of two or more coupled high temperature superconductor self-resonant coils, comprising varying the distance between the centers of the two or more coils. In particular, the resonance frequency of the fundamental symmetric mode increases as the distance between the centers of the two or more coils increases and the resonance frequency of the fundamental symmetric mode decreases as the distance between the centers decreases.

The two or more coils are preferably essentially identical, and most preferably, they are identical. The two or more coils are preferably parallel, and they are preferably surface or planar coils.

This invention also provides a frequency detection system, e.g. a nuclear quadrupole resonance detection system, comprised of two or more coupled high temperature superconductor coils and means to vary the distance between the coils.

DETAILED DESCRIPTION OF THE PREFERRED EMBODIMENTS

The resonance frequency of the fundamental symmetric mode of two or more coupled HTS self-resonant coils can be used to detect the presence of signals of that frequency. It has now been observed that when the distance between the centers of two or more HTS coils is sufficiently small the resonance frequency of the fundamental symmetric mode can be readily tuned, and having been thus tuned can be used to detect the presence of signals.

This invention provides a method for tuning the resonance frequency of the fundamental symmetric mode by varying the distance between the centers of the two or more coils. As the distance between the centers of the two or more coils is increased, the resonance frequency is increased. As the distance between the centers of the two or more coils is decreased, the resonance frequency is decreased. This tuning is accomplished with little degradation or reduction, i.e. less than a 20% change, in the quality factor ("Q") of the coil.

The two or more HTS coils are essentially identical if they are not actually identical. Coils are essentially identical when they are, if not actually identical, as nearly alike in every respect as possible. In essentially identical coils, the materials from which they have been fabricated, the process by which they have been fabricated, and the properties they exhibit are as nearly alike as possible. Preferably, however, the coils are actually identical.

The coil preferred for use in this invention is a planar or surface coil that has an HTS coil configuration on only one side of a substrate or, more preferably, has identical, or essentially identical, HTS coil configurations on both sides of the substrate. The coils used in the examples have essentially identical, if not identical, HTS coil configurations on both sides of the substrate. The plane of a coil is the plane of the substrate supporting the HTS coil configuration.

Figure 1A:
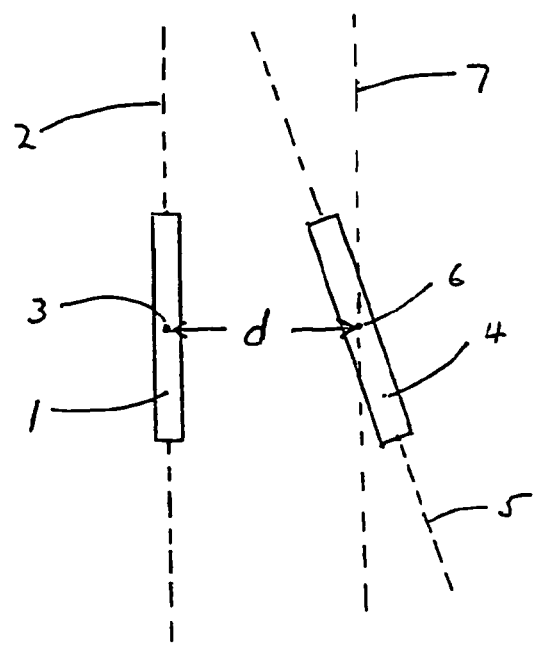
FIGS. 1a-1c show a cross-sectional drawing of two coupled HTS coils in various configurations.

A schematic cross-sectional drawing of two coupled HTS coils is shown in FIG. 1a. The first coil 1 lies in plane 2, which is perpendicular to the plane of the drawing. First coil 1 has a coil center 3 that lies in plane 2. The second coil 4 lies in plane 5, which is not necessarily perpendicular to the plane of the drawing, and is not parallel to plane 2. Second coil 4 has a coil center 6 that lies in plane 5. Plane 7 is parallel to plane 2 and also contains coil center 6. The distance d is the separation between coil center 3 and coil center 6. The line connecting the centers 3 and 6 is perpendicular to planes 2 and 7.

Distance d can be increased, thereby increasing the fundamental frequency, by increasing the separation between planes 2 and 7; by moving second coil 4 up or down vertically in plane 7 in the plane of FIG. 1a; by moving second coil 4 perpendicular to the plane of FIG. 1a but still in plane 7; or by a combination of such movements that results in an increase in the distance of separation between coil center 3 and coil center 6.

Figure 1B:
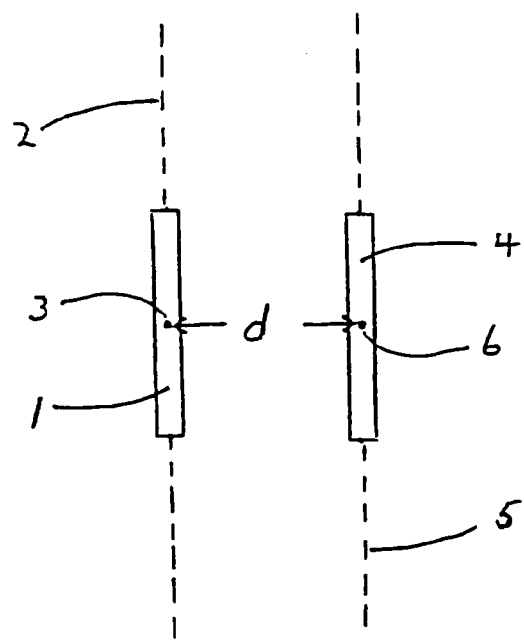

FIG. 1b is a cross-sectional drawing of two HTS coils when they are parallel, i.e. when plane 5 has been rotated into plane 7, and coaxial, i.e. the line connecting their centers is perpendicular to the planes of the coils (planes 2 and 5). The first coil 1 again lies in plane 2, which is perpendicular to the plane of the drawing, and has a coil center 3 that lies in plane 2. The second coil 4 lies in plane 5, which is now parallel to plane 2. Second coil 4 has a coil center 6 that lies in plane 5. The distance d is the separation between coil center 3 and coil center 6. Distance d can be increased, thereby increasing the frequency of the fundamental symmetric mode, by increasing the separation between planes 2 and 5; by moving second coil 4 up or down vertically in plane 5 in the plane of the drawing; by moving second coil 4 horizontally in plane 5, i.e. perpendicular to the plane of FIG. 1b; or by a combination of such movements that results in an increase in the distance of separation between coil center 3 and coil center 6.

In one embodiment, a case, for example, when the two coils are parallel, the method of the invention for tuning the frequency of the fundamental symmetric mode is useful when the distance between the planes of the coils, i.e. plane 2 and plane 5 of FIG. 1b, is less than about 50% of the radius of the coils. As the distance between planes 2 and 5 increases from essentially zero to about 50% of the radius of the coils, the resonance frequency of the fundamental symmetric mode increases; as the distance between planes 2 and 5 decreases from about 50% of the radius of the coils to about zero, the resonance frequency of the fundamental symmetric mode decreases.

In this embodiment, when the two coils are not only parallel but are in the coaxial configuration as shown in FIG. 1b, the resonance frequency of the fundamental symmetric mode can be tuned by varying the distance between the centers of the coils, i.e. between centers 3 and 6, from essentially zero up to a distance equal to about 50% of the radius of the coils. Typically, a variation in distance over this range, i.e. increasing from 0 to about 50% of the radius of the coils, will result in about a 15-20% increase in the resonance frequency of the fundamental symmetric mode with little degradation in Q.

Figure 1C:
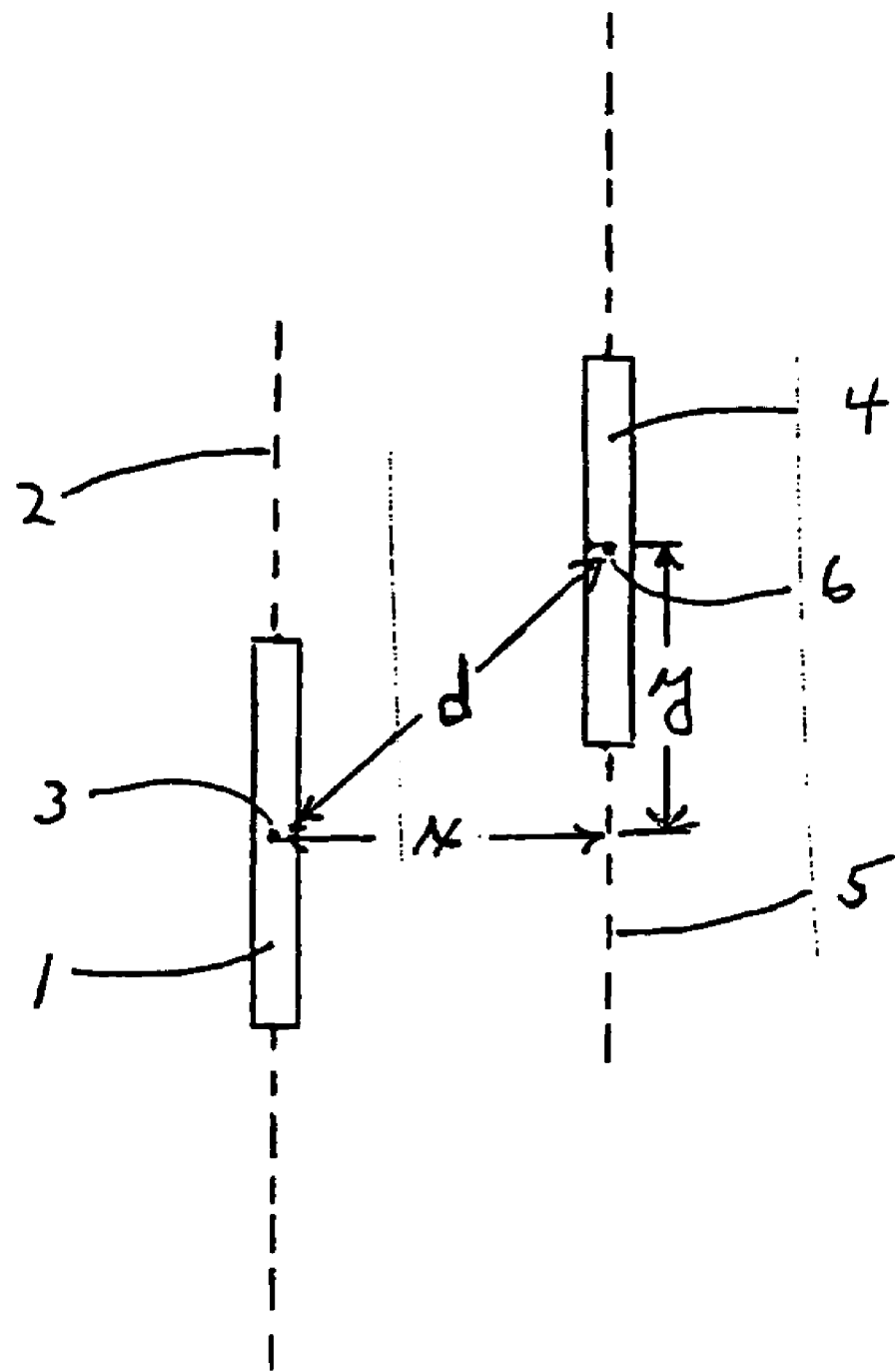

FIG. 1c is a cross-sectional drawing of two HTS coils when they are parallel, i.e. when plane 2 is parallel to plane 5, but the coils are not coaxial, i.e. the line connecting the centers of the coils is not perpendicular to the plane of each coil. The first coil 1 again lies in plane 2, which is perpendicular to the plane of the drawing and has a coil center 3 that lies in plane 2. The second coil 4 lies in plane 5, which is parallel to plane 2 and is perpendicular to the plane of the drawing. Second coil 4 has a coil center 6 that lies in plane 5. The distance d is the separation between coil center 3 and coil center 6. However, as shown in FIG. 1c, the line connecting the centers 3 and 6 is no longer perpendicular to planes 2 and 5. Parallel planes 2 and 5 are separated by a distance x. The vertical or off-axis displacement of second coil 4 from the coaxial position is shown as y.

In this embodiment, when the two coils are parallel but are not in a coaxial configuration (as shown in the configuration in FIG. 1c), the resonance frequency of the fundamental symmetric mode can be tuned by varying the distance d between the centers of the coils, i.e. between centers 3 and 6. Distance d can be varied, thereby varying the resonance frequency of the fundamental symmetric mode, by varying x and/or y. As indicated above, the method of the invention for tuning the resonance frequency of the fundamental symmetric mode is useful when x is in the range of from 0 to about 50% of the radius of the coils. The amount that y is varied depends upon the magnitude of x. As an example, when x is about 5% of the radius of the coils, the vertical displacement y can be as large as the radius of the coils. There is typically about a 25-30% increase in the resonance frequency of the fundamental symmetric mode with little degradation in Q when x is about 5% of the radius of the coils and y is increased from zero to about the radius of the coils.

In this embodiment, lateral displacements and other off-axis displacements in any other direction within the plane of the second coil will have the same effect as, and are equivalent to, the vertical off-axis displacement described above as long as the planes of the coils are parallel and the distance between the planes is the same.

To decrease resonance frequency, the distance between coils can be decreased by performing the reverse of the movements described above by which the distance was increased.

It is preferred that the coils be parallel, but the coils may be non-parallel, i.e. the plane of one coil may be rotated with respect to the plane of another coil by a small angle. As a result, in yet another embodiment, when the coils are not exactly parallel, such as the result of imperfections in the alignment process, the same magnitudes of change in the resonance frequency occur when the two or more coils are subjected to any of the types of movements described above.

No matter how many coils are coupled, the distance between adjacent coils can be changed by varying the distance between the planes of the coils, i.e., lateral displacement of coaxial coils, or by adjusting the off-axis displacement of one or more coils with respect to an adjacent coil.

The distance between the centers of the coils can be changed by any convenient means. Means to vary the distance between coils include changing both x and y, or changing the distance in any other direction, using micropositioners in order to be able to make a continuous variation in distance between the centers of the two or more coils and therefore make a continuous tuning of the resonance frequency of the fundamental symmetric mode.

The frequency of the fundamental symmetric mode of the coupled high temperature superconductor coils is lower than the resonance frequency of a single coil. The reduction in the frequency of the fundamental symmetric mode of the coupled high temperature superconductor coils relative to the resonance frequency of a single coil is greater the larger the number of coils used. Two coupled coils will provide a fundamental symmetric mode frequency reduced by a certain percentage from the resonance frequency of a single coil. The use of three such coils provides a fundamental symmetric mode frequency reduced by a greater percentage and the use of four such coils provides a fundamental symmetric mode frequency reduced by a still greater percentage. These greater reductions are important. The frequency tuning range of the coupled coils is set at the upper end by the resonance frequency of a single coil and at the lower end by the fundamental symmetric mode frequency of the coupled coils with essentially no separation between the coils. Thus the use of two coupled coils provides a certain frequency tuning range and the use of three, four or more coupled coils provides increased frequency tuning ranges. The range is increased as the number of coils used is increased.

The method of this invention for tuning the resonance frequency of the fundamental symmetric mode of two or more coupled high temperature superconductor self-resonant coils is useful when the coupled coils are used in a detection system for detecting frequencies. The ability to tune frequencies is especially valuable in a nuclear quadrupole resonance (NQR) detection system that is being used to detect the presence of a particular chemical compound where there is a specificity of NQR frequencies as to the particular compound.

An NQR detection system comprised of two or more coupled high temperature superconductor self-resonant coils, and means to vary the distance between them, can be used to detect the presence of chemical compounds for any purpose, but is particularly useful for detecting the presence of controlled substances such as explosives, drugs or contraband of any kind. Such an NQR detection system could be usefully incorporated into a safety system, a security system, or a law enforcement screening system. For example, these systems can be used to scan persons and their clothing, carry-on articles, luggage, cargo, mail and/or vehicles. They can also be used to monitor quality control, to monitor air or water quality, and to detect biological materials.

In the detection system of the invention, the two or more coupled high temperature superconductor self-resonant coils can be used to both transmit and receive signals, so that in an NQR detection system the two or more coupled high temperature superconductor self-resonant coils can be used to both excite the NQR as well as to detect the resulting NQR frequency. Preferably, the two or more coupled high temperature superconductor self-resonant coils are used solely as sensors, i.e., to detect the NQR frequency, and one or more other coils are used to transmit the RF signal and excite the NQR.

High temperature superconductors are superconducting above about 77K, or at temperatures that may be reached by cooling with liquid nitrogen. The high temperature superconductor used to form the HTS coils is preferably selected from the group consisting of $YBa_2Cu_3O_7$, $Tl_2Ba_2CaCu_2O_8$, $TlBa_2Ca_2Cu_3O_9$, $(TlPb)Sr_2CaCu_2O_7$ and $(TlPb)Sr_2Ca_2Cu_3O_9$. Most preferably, the high temperature superconductor is $Tl_2Ba_2CaCu_2O_8$.

Figure 2:
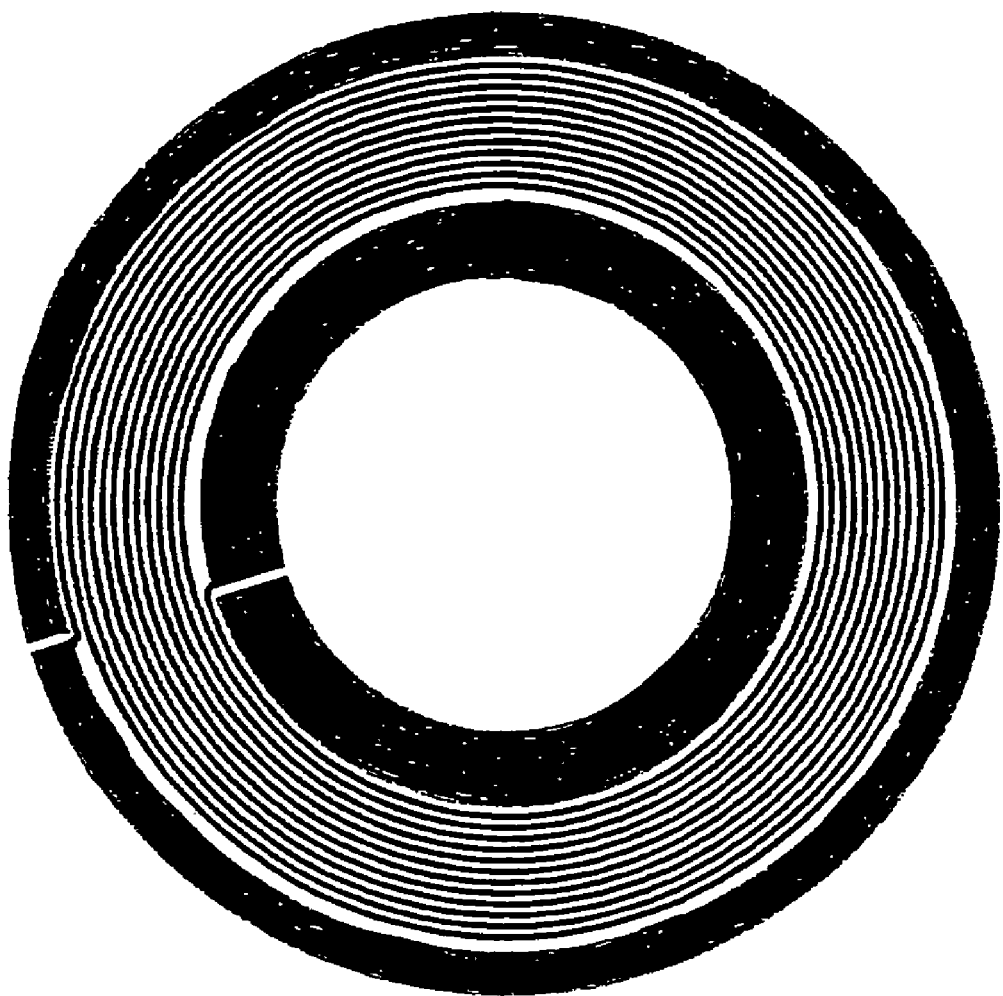
FIG. 2 shows the top view of the HTS coil configuration of the two coupled HTS coils used in Examples 1, 2 and 3.

The coils could, for example, be constructed from a single crystal sapphire substrate with a $CeO_2$ buffer layer and a high temperature superconductor pattern of the configuration shown in FIG. 2 centered on the $CeO_2$ buffer layer on each side of the single crystal sapphire substrate. Or, they could, in a further example, be constructed from a single crystal $LaAlO_3$ substrate and a high temperature superconductor pattern of the configuration shown in FIG. 2 centered on each side of the single crystal $LaAlO_3$ substrate.

The advantageous effects of this invention are demonstrated by a series of examples, as described below. The embodiments of the invention on which the examples are based are illustrative only, and do not limit the scope of the invention.

EXAMPLES OF THE INVENTION

Example 1

This example uses two HTS $Tl_2Ba_2CaCu_2O_8$ coils that are essentially identical, if not actually identical, on sapphire ($Al_2O_3$) substrates, each with the coil design configuration shown in FIG. 2 on both sides of each substrate, to demonstrate the change in the fundamental symmetric mode resonance frequency of the two coupled coils as the distance between the centers is changed.

A clean, polished single crystal sapphire substrate with a radius of 2 inches (5.1 cm) and an approximate thickness of 0.018 inches (0.46 mm) was obtained from Union Carbide Corp. An epitaxial $CeO_2$ buffer layer was grown on both sides of the substrate by off-axis sputter deposition with the substrate temperature held in the range of about 700-800° C. Off-axis magnetron sputtering of a Ba:Ca:Cu oxide target was used to deposit, at room temperature (about 20° C.), an amorphous precursor Ba:Ca:Cu oxide film on the $CeO_2$ buffer layer on both sides of the substrate. This amorphous Ba:Ca:Cu oxide film was about 550 nm thick and had a stoichiometry of about 2:1:2. The precursor film was then thallinated by annealing it in air for about 45 minutes at 850° C. in the presence of a powder mixture of $Tl_2Ba_2Ca_2Cu_3O_{10}$ and $Tl_2O_3$. When this powder mixture is heated, $Tl_2O$ evolves from the powder mixture, diffuses to the precursor film and reacts with it to form the $Tl_2Ba_2CaCu_2O_8$ phase.

The sample was then coated with photoresist on both sides and baked. A coil design mask with the design shown in FIG. 2 was prepared. The coil had an inner radius of about 10.5 mm and an outer radius of about 22.5 mm. The outermost HTS ring of the coil was about 2 mm wide and the innermost HTS ring was about 3.5 mm wide. The intermediate HTS rings were about 250 µm wide with about 250 µm gaps between the rings. The coil design mask was then centered on the photoresist covering the $Tl_2Ba_2CaCu_2O_8$ film on the front side of the substrate and exposed to ultraviolet light. The coil design mask was then centered on the photoresist covering the $Tl_2Ba_2CaCu_2O_8$ film on the back side of the substrate and exposed to ultraviolet light. The resist was then developed on both sides of the substrate and the portion of the $Tl_2Ba_2CaCu_2O_8$ film exposed when the resist was developed was etched away by argon beam etching. The remaining photoresist layer was then removed by an oxygen plasma. The result was a coil comprised of the single crystal sapphire substrate with a $CeO_2$ buffer layer and a high temperature superconductor $Tl_2Ba_2CaCu_2O_8$ pattern of the configuration shown in FIG. 2 centered on the $CeO_2$ buffer layer on each side of the single crystal sapphire substrate. The process was repeated in essentially the same way to produce a second coil. Each of the two coils had a resonance frequency of 4696 kHz when immersed in liquid nitrogen held in a Nalgene® (Nalge Nunc International, Rochester, N.Y.) dewar as determined by the measuring technique described below.

The two coils were placed with the planes of the coils parallel and as close together as possible in a co-axial configuration, i.e., with the line connecting the centers perpendicular to the two planes of the coils. The coils were immersed in liquid nitrogen held in a Nalgene® dewar. A pick-up coil comprised of a loop of copper wire was placed about 1 inch (2.5 cm) away from the coils with the plane of the pick-up coil parallel to the planes of the coils. The pick-up coil was formed by removing the outer jacket and dielectric spacer from a piece of 0.080 inch (2 mm) coax cable. The loop was formed by bending the inner conductor into a circle and soldering it to the outer jacket of the coax cable just outside the point where the jacket and dielectric were removed. The pick-up coil is connected to an Agilent 8753 Vector Network Analyzer (Agilent Technologies, Palo Alto, Calif.). The frequency was swept and the resonance frequency and Q measured as the distance between the centers of the coils was increased from essentially zero, i.e., the two coils were placed as close to one another as possible, to 6.1 mm while maintaining the co-axial configuration. Referring to the configuration of FIG. 1c, for this co-axial separation, y=0 and x takes the values between 0 and 6.1 mm, about 27% of the radius of the coils. At essentially zero separation, i.e., x=0, the fundamental symmetric mode resonance frequency was 3430 kHz and the Q=14,000. When the separation was increased to 6.1 mm the fundamental symmetric mode resonance frequency was 4113 kHz and the Q=14,000. This is a 20% increase in the fundamental symmetric mode resonance frequency with no significant reduction in Q.

Figure 3:
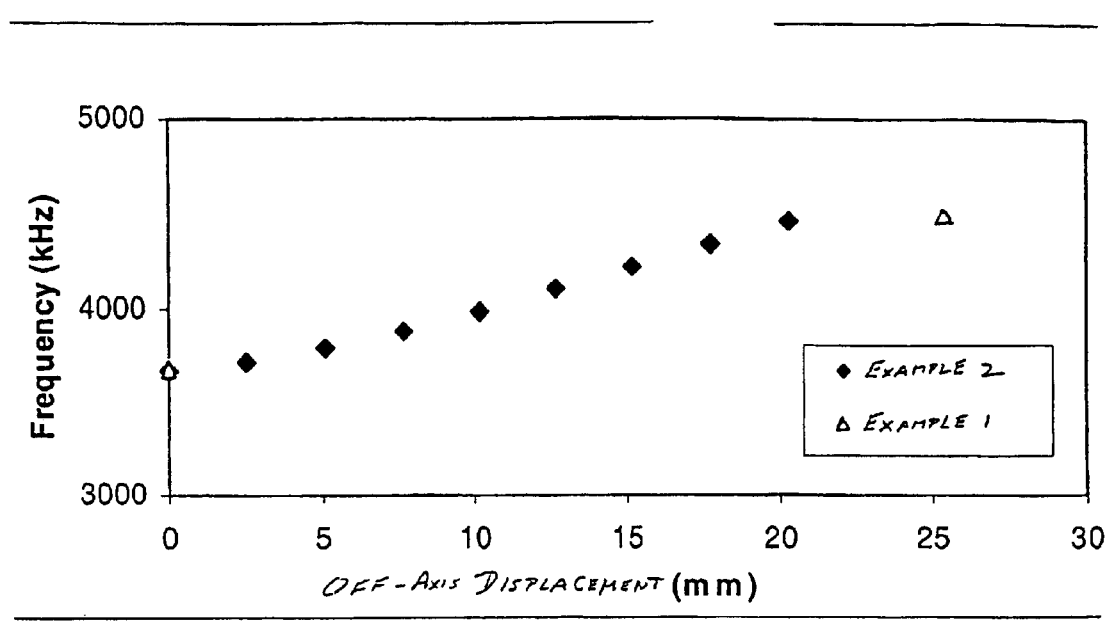
FIG. 3 shows the fundamental symmetric mode resonance frequency tuning results obtained in Examples 1 and 2 by varying the off-axis displacement of one of the two coupled HTS coils with respect to the other coil.

The two coils were then placed with the planes of the coils parallel in a co-axial configuration, i.e., with the line connecting the centers perpendicular to the two planes of the coils. Again referring to FIG. 1c, the separation of the centers x was 1 mm, about 4.5% of the radius of the coils and y=0. The second coil was then moved vertically off-axis with respect to the first coil until the center was 1 inch (25.4 mm) from its original co-axial position, i.e., y=25.4 mm, about the radius of the coils. At y=0, the fundamental symmetric mode resonance frequency was 3682 kHz and the Q=14,400. When the off-axis displacement was 25.4 mm, the fundamental symmetric mode resonance frequency was 4489 kHz and the Q=14,000. This is about a 30% increase in the fundamental symmetric mode resonance frequency with a change in Q of less than 3%. These two results are shown as the triangular-shaped points in FIG. 3.

These results demonstrate the method for tuning the fundamental symmetric mode resonance frequency of two essentially identical coupled high temperature superconductor self-resonant coils by mechanically displacing one coil with respect to the other.

Example 2

This example uses two HTS $Tl_2Ba_2CaCu_2O_8$ coils that are essentially identical, if not actually identical, on sapphire ($Al_2O_3$) substrates, each with the coil design configuration shown in FIG. 2 on both sides of each substrate, to demonstrate the change in the fundamental symmetric mode resonance frequency of the two coupled coils as the distance between the centers is changed. These coils were made essentially following the method described in Example 1.

The two coils were then placed with the planes of the coils parallel in a co-axial configuration, i.e., with the line connecting the centers perpendicular to the two planes of the coils. Again referring to FIG. 1c, the separation of the centers x was 1 mm, about 4.5% of the radius of the coils and y=0. The second coil was then moved vertically off-axis with respect to the first coil by means of a micrometer until the center was 20.3 mm from its original co-axial position, i.e., y=20.3 mm. The increase in the fundamental symmetric mode resonance frequency as a function of off-axis displacement is plotted as the diamond-shaped points in FIG. 3.

These results demonstrate the method for tuning the fundamental symmetric mode resonance frequency of two coupled essentially identical high temperature superconductor self-resonant coils by mechanically displacing one coil with respect to the other.

Example 3

This example uses two HTS $Tl_2Ba_2CaCu_2O_8$ coils that are essentially identical, if not actually identical, on $LaAlO_3$ substrates, each with the coil design configuration shown in FIG. 2 on both sides of each substrate, to demonstrate the change in the fundamental symmetric mode resonance frequency of the two coupled coils as the distance between the centers of the coils is changed. The two coils were made essentially by the method described in Example 1 except that a clean, polished single crystal $LaAlO_3$ substrate (obtained from Litton Airtron, Morris Plains, N.J.) was used instead of the clean, polished single crystal sapphire substrate and there was no $CeO_2$ buffer layer. Each clean, polished single crystal $LaAlO_3$ substrate had a radius of 2 inches (5.1 cm) and a thickness of approximately 0.020 inches (0.51 mm). Each of the two coils was comprised of the single crystal $LaAlO_3$ substrate and a high temperature superconductor $Tl_2Ba_2CaCu_2O_8$ pattern of the configuration shown in FIG. 2 centered on each side of the single crystal $LaAlO_3$ substrate.

The two coils were placed with the planes of the coils parallel in a co-axial configuration, i.e., with the line connecting the centers perpendicular to the two planes of the coils. Again referring to FIG. 1c, the separation of the centers x was 40 mil (1 mm), about 4.5% of the radius of the coils. Measurements were taken when y=0 and when the second coil was moved vertically with respect to the first coil until the center was 1 inch (25.4 cm) from its original co-axial position. At y=0, the fundamental symmetric mode resonance frequency was 2668 kHz and the Q=21,000. When the separation was increased to 1 inch (25.4 mm), the fundamental symmetric mode resonance frequency was 3446 kHz and the Q=20,000. This is about a 29% increase in the fundamental symmetric mode resonance frequency resonance with only about a 5% reduction in Q.

These results demonstrate the method for tuning the fundamental symmetric mode resonance frequency of two coupled essentially identical high temperature superconductor self-resonant coils by mechanically displacing one coil with respect to the other.

Example 4

Sonnet EM Software, obtained from Sonnet Software, Inc., Liverpool, N.Y. 13088, was used to simulate the performance of coupled coils to further demonstrate the advantages of using 2, 3 or 4 coupled coils as well as to further demonstrate the frequency tuning afforded by the use of two or more coupled coils. The following model was used. The substrate had a thickness of 0.5 mm and a dielectric constant $\in$=24. The substrate had a front side and a back side. A 36 mm×36 mm square coil, with outermost turn 2 mm wide, innermost turn 3.25 mm wide and all other turns and spacings 0.25 mm wide was simulated on both sides of the substrate.

The resonance frequency of one such square coil was 4.95 MHz. Two, three and four such coils were coupled in a coaxial configuration with the planes of the coils parallel and the fundamental symmetric mode frequency determined for various separations between the coils. When two coupled coils were used the separation was the distance between the substrates of the two coils. When three or four coupled coils were used the separation was the distance between the substrates of adjacent coils. The results obtained are shown in Table I. "FSM frequency" is the fundamental symmetric mode frequency. "FSM Frequency Reduction" is the fractional reduction in the FSM frequency relative to the single coil resonance frequency. For example, the FSM frequency of two coupled coils separated by 0.05 mm is 3.29 MHz. This is 34% lower than the single coil resonance frequency 4.95 MHz and the FSM Frequency Reduction is listed as the fractional reduction, i.e., 0.34.

TABLE I

| Number of Coils | Separation (mm) | FSM Frequency (MHz) | FSM Frequency Reduction |
|---|---|---|---|
| 2 | 0.05 | 3.29 | 0.34 |
| 2 | 0.1 | 3.45 | 0.30 |
| 2 | 0.25 | 3.59 | 0.27 |
| 2 | 0.5 | 3.69 | 0.26 |
| 3 | 0.1 | 2.87 | 0.42 |
| 3 | 0.5 | 3.14 | 0.37 |
| 4 | 0.5 | 2.83 | 0.43 |

Figure 4:
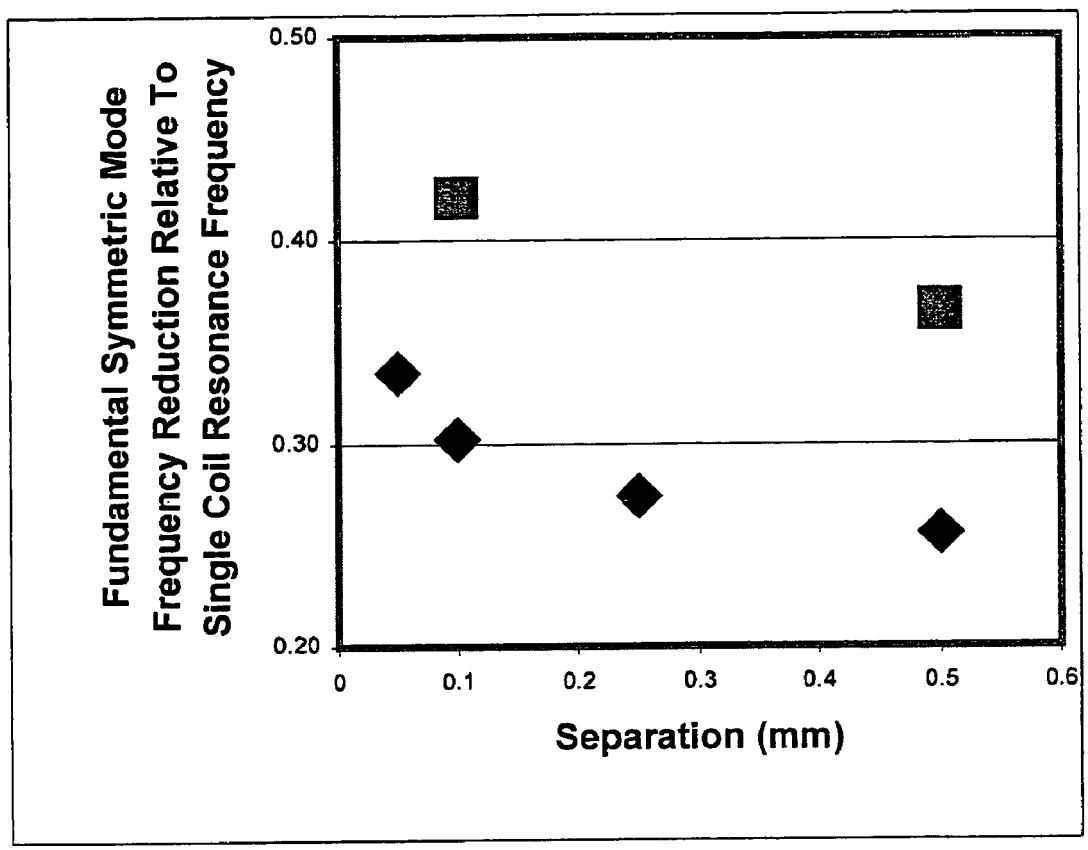
FIG. 4 shows the fundamental symmetric mode frequency reduction relative to a single coil resonance frequency as found in Example 4 by varying the separation of two coupled HTS coils and of three coupled HTS coils.

The FSM Frequency Reduction is plotted in FIG. 4 as a function of separation for two coupled coils (points on the graph are indicated by diamonds) and three coupled coils (points on the graph are indicated by squares). The reduction is smaller, i.e., the frequency is higher, the larger the separation as discussed previously. Greater reductions are achieved with three coils than with two coils.

Figure 5:
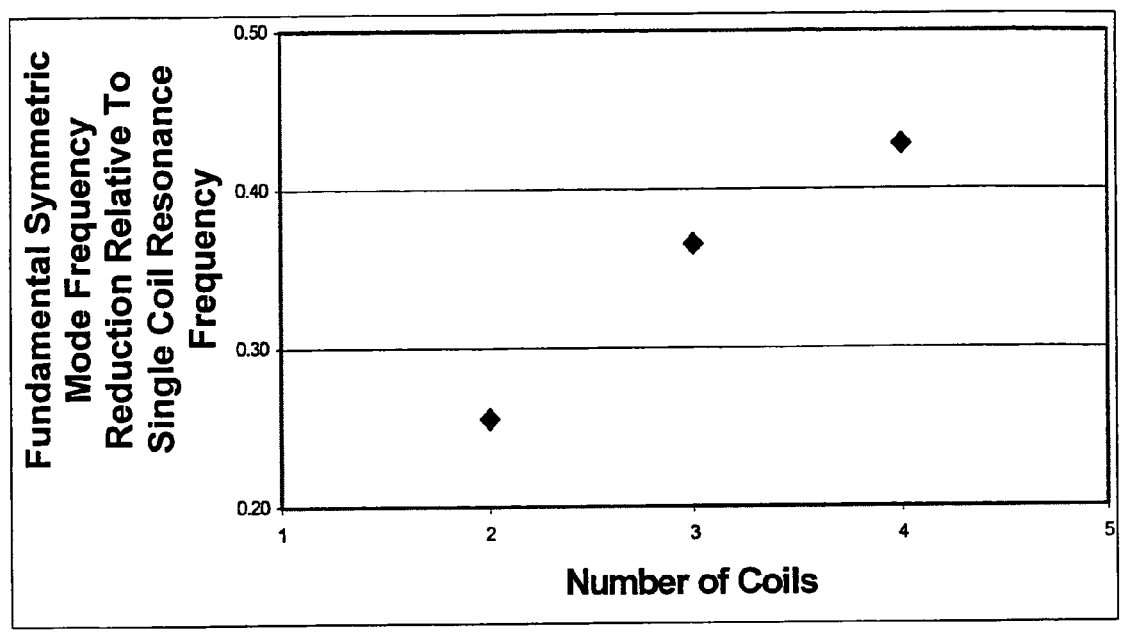
FIG. 5 shows the fundamental symmetric mode frequency reduction relative to a single coil resonance frequency as found in Example 4 for two, three and four coupled HTS coils when the separation between the planes of adjacent coils is 0.5 mm.

The FSM Frequency Reduction is plotted in FIG. 5 as a function of the number of coupled coils. The separation between substrates of adjacent coils was 0.5 mm. Greater reductions and therefore greater frequency tuning ranges are achieved the larger the number of coupled coils.

Example 5

This example uses three HTS $Tl_2Ba_2CaCu_2O_8$ coils that are essentially identical on single crystal $LaAlO_3$ substrates to demonstrate the greater reduction in the fundamental symmetric mode resonance frequency achieved with three coupled coils compared to that achieved with two coupled coils.

The three coils were prepared essentially as described in Example 3 except that the coil design configuration was altered so that the inner radius was about 3.5 mm. The outer radius was about 22.5 mm as before. The outermost HTS ring of the coil was 1.88 mm wide and the innermost HTS ring was 3.38 mm wide. The 19 intermediate HTS rings were about 250 µm wide with about 250 µm gaps between the rings. In addition, each coil was coated with a thin protective layer of Teflon™ AF.

The resonance frequency of each of the three coils was 2.43 MHz. When two of the coils were placed with no deliberate separation between them, except for the Teflon™ AF layers, the fundamental symmetric mode frequency was 1.50 MHz, 38% lower than the single coil resonance frequency. When all three coils were placed with no deliberate separation between them, except for the Teflon™ AF layers, the fundamental symmetric mode frequency was 1.02 MHz, 58% lower than the single coil resonance frequency.

This demonstrates the greater reduction in the fundamental symmetric mode resonance frequency achieved with three coupled coils compared to that achieved with two coupled coils. The frequency tuning range is increased accordingly.

What is claimed is:

1. A frequency detection system comprising:
   two essentially identical coupled planar high temperature superconductor self-resonant coils, said coils being able to detect signals having a predetermined fundamental symmetric mode resonance frequency, wherein said two coils are parallel; and
   means for tuning the resonance frequency of said coupled coils to said fundamental symmetric mode frequency by varying one or more distances between said coils,
   wherein said means comprises micropositioners to vary the distance between the planes of said two coils from essentially zero to about 50% of the radius of the coils.

2. The frequency detection system of claim 1, wherein said frequency detection system is a nuclear quadrupole resonance detection system.

3. A frequency detection system comprising:
   two essentially identical coupled planar high temperature superconductor self-resonant coils, said coils being able to detect signals having a predetermined fundamental symmetric mode resonance frequency, wherein said two coils are parallel; and
   means for tuning the resonance frequency of said coupled coils to said fundamental symmetric mode frequency by varying one or more distances between said coils,
   wherein said means comprises micropositioners to vary the off-axis displacement of one of said two coils with respect to the other coil,
   wherein the planes of the two coils are separated by a distance of from essentially zero to about 50% of the radius of said coils.

4. The frequency detection system of claim 3, wherein said frequency detection system is a nuclear quadrupole resonance detection system.

5. A frequency detection system comprising:
   two essentially identical coupled planar high temperature superconductor self-resonant coils, said coils being able to detect signals having a predetermined fundamental symmetric mode resonance frequency, wherein said two coils are parallel; and
   means for tuning the resonance frequency of said coupled coils to said fundamental symmetric mode frequency by varying one or more distances between said coils,
   said means comprises micropositioners to vary said distance between said planes of said two coils from essentially zero to about 50% of the radius of said coils and to vary the off-axis displacement of one of said two coils with respect to the other coil from essentially zero to about the radius of said two coils.

6. The frequency detection system of claim 5, wherein said frequency detection system is a nuclear quadrupole resonance detection system.

7. A frequency detection system comprising:
   three or four essentially identical coupled planar high temperature superconductor self-resonant coils, said coils being able to detect signals having a predetermined fundamental symmetric mode resonance frequency, wherein said three or four coils are parallel; and
   means for tuning the resonance frequency of said coupled coils to said fundamental symmetric mode frequency by varying one or more distances among said coils,
   said means comprises micropositioners to vary the off-axis displacements of all of said three or four coils with respect to the other coils.

8. The frequency detection system of claim 7, wherein said frequency detection system is a nuclear quadrupole resonance detection system.

9. A frequency detection system comprising:
   three or four essentially identical coupled planar high temperature superconductor self-resonant coils, said coils being able to detect signals having a predetermined fundamental symmetric mode resonance frequency, wherein said three or four coils are parallel; and
   means for tuning the resonance frequency of said coupled coils to said fundamental symmetric mode frequency by varying one or more distances between said coils,
   wherein said means comprises micropositioners to vary the distance between the planes of said three or four coils and to vary the off-axis displacements of all of said three or four coils with respect to the other coils.

10. The frequency detection system of claim 9, wherein said frequency detection system is a nuclear quadrupole resonance detection system.

* * * * *